(12) United States Patent
Kojima et al.

(10) Patent No.: US 7,393,987 B2
(45) Date of Patent: Jul. 1, 2008

(54) PROCESS FOR PRODUCING ADAMANTANE

(75) Inventors: Akio Kojima, Chiba (JP); Masao Saito, Chiba (JP); Shinji Miyamoto, Chiba (JP); Jun Mase, Chiba (JP); Toyozo Fujioka, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 4 days.

(21) Appl. No.: 10/582,607

(22) PCT Filed: Dec. 16, 2004

(86) PCT No.: PCT/JP2004/018825

§ 371 (c)(1),
(2), (4) Date: Jun. 12, 2006

(87) PCT Pub. No.: WO2005/058779

PCT Pub. Date: Jun. 30, 2005

(65) Prior Publication Data

US 2007/0156002 A1    Jul. 5, 2007

(30) Foreign Application Priority Data

Dec. 17, 2003    (JP) .............................. 2003-419017

(51) Int. Cl.
 *C07C 13/28* (2006.01)
(52) U.S. Cl. ..................................... 585/352
(58) Field of Classification Search ................... 585/352
 See application file for complete search history.

(56) References Cited

U.S. PATENT DOCUMENTS

| 6,784,328 | B2 | 8/2004 | Kojima et al. |
| 7,019,183 | B2 | 3/2006 | Kojima et al. |
| 2003/0018226 | A1 | 1/2003 | Kojima et al. |
| 2004/0171902 | A1 | 9/2004 | Kojima et al. |
| 2006/0111596 | A1 | 5/2006 | Mase et al. |

FOREIGN PATENT DOCUMENTS

| JP | 52052888 A | * | 4/1977 |
| WO | 02/48076 | | 6/2002 |
| WO | 02/48077 | | 6/2002 |
| WO | 02/062731 | | 8/2002 |

OTHER PUBLICATIONS

U.S. Appl. No. 10/590,995, filed Aug. 29, 2006, Mase et al.
U.S. Appl. No. 10/942,098, filed Sep. 16, 2004, Kojima et al.

* cited by examiner

*Primary Examiner*—Thuan Dinh Dang
(74) *Attorney, Agent, or Firm*—Oblon, Spivak, McClelland, Maier & Neustadt, P.C.

(57) ABSTRACT

The present invention provides a process of an industrially advantageous production of high-purity adamantane at a low cost and with a high efficiency by isomerizing trimethylenenorbornane contained in a raffinate obtained from a platfinate.

4 Claims, No Drawings

PROCESS FOR PRODUCING ADAMANTANE

TECHNICAL FIELD

The present invention relates to a process for producing inexpensive, high-purity adamantane. More specifically, the present invention is directed to an industrial process for producing high-purity adamantane at a low cost and with a high efficiency by isomerizing trimethylenenorbornane contained in a raffinate obtained from a platfinate.

BACKGROUND ART

Adamantane is a stable, highly symmetrical compound in which four cyclohexane rings are condensed to form a cage-like structure. It is known that adamantane, which has such a specific adamantane skeleton and which shows peculiar functions, is useful as a lubricant or as a raw material for agricultural and medical materials and highly functional industrial materials.

As a method for producing adamantane, a process is generally adopted in which trimethylenenorbornane obtained by hydrogenating dicyclopentadiene is isomerized.

In such an isomerization reaction, aluminum chloride is generally used as a catalyst.

The yield of adamantane produced by using aluminum chloride as a catalyst is about 50% by mass (for example, Patent Documents 1 and 2). In this case, the catalyst must be used in a large amount and further cannot be reused because it forms complexes with heavy components during the reaction.

Therefore, the known method produces a large amount of waste aluminum, disposal of which causes problems of environmental pollution.

In addition, since the use of aluminum chloride causes coloring of the adamantane product, it is necessary to conduct a recrystallization step and a decoloring step using, for example, active carbon. Thus, a problem is caused that post treatments become inevitably troublesome.

There is also known a solid catalyst which contains an active metal such as platinum, rhenium, nickel or cobalt carried on a cation-exchanged zeolite by an impregnation process (for example, Patent Document 3).

A process for producing adamantane using the above solid catalyst in which an active metal such as platinum, rhenium, nickel or cobalt is carried on a cation-exchanged zeolite by an impregnation process can solve the above problems caused in the case where aluminum chloride catalyst is used.

Patent Document 1: JP-A-Shou-50-71663
Patent Document 2: JP-A-2000-143556
Patent Document 3: JP-B-Shou-52-2909

The above-described conventional methods using aluminum chloride catalyst or a solid catalyst, however, have a problem that the production of adamantane requires unavoidably a high cost because trimethylenenorbornane used as a starting material should be obtained by hydrogenating dicyclopentadiene which is expensive.

DISCLOSURE OF THE INVENTION

In this circumstance, an object of the present invention is to provide an industrially advantageous process for producing high-purity adamantane at a low cost and with a high efficiency.

The present inventors have made earnest studies with a view toward accomplishing the above object. As a result, the inventors have paid their attention to the fact that trimethylenenorbornane is contained in a raffinate obtained from a platfinate and have found that the object can be fulfilled by using such trimethylenenorbornane as a starting material.

The present invention has been completed on the basis of such findings.

Thus, the present invention provides:

(1) A process for producing adamantane, characterized by isomerizing trimethylenenorbornane contained in a raffinate obtained from a platfinate;
(2) A process for producing adamantane as recited in (1) above, wherein the isomerization is performed after concentrating trimethylenenorbornane contained in the raffinate;
(3) A process for producing adamantane as recited in (2) above, wherein the isomerization is performed after concentrating trimethylenenorbornane contained in the raffinate and after reducing the amount of alkyl group-containing trimethylenenorbornane; and
(4) A process for producing adamantane as recited in any one of (1) to (3) above, wherein the isomerization is carried out by using a solid catalyst.

PREFERRED EMBODIMENT FOR CARRYING OUT THE INVENTION

In the process for producing adamantane according to the present invention, trimethylenenorbornane contained in a raffinate obtained from a platfinate is used as a starting material.

The term "platfinate" herein is a fraction obtainable by hydrogenating olefins contained in pyrolysis gasoline derived from steam cracking of naphtha, the hydrogenated product being thereafter treated for removing a light gas stream therefrom.

The term "raffinate" herein is a residual fraction obtained by extracting an aromatic fraction contained in the above-described platfinate with sulforane, etc. The raffinate contains trimethylenenorbornane, methyltrimethylenenorbornane and, else, naphthenes having 5 to 11 carbon atoms and aromatics having 6 to 11 carbon atoms.

Accordingly, dicyclopentadiene contained in the pyrolysis gasoline has been hydrogenated and converted to trimethylenenorbornane which is contained in the platfinate and, further, in the raffinate.

Namely, in the present invention, trimethylenenorbornane contained in the raffinate which has not been utilized conventionally except as a fuel, etc. is effectively utilized.

The raffinate may be used as such but preferably used after concentrating the trimethylenenorbornane from the standpoint of production efficiency.

As a method for concentrating trimethylenenorbornane contained in the raffinate, atmospheric distillation or vacuum distillation may be preferably used.

By reducing the content of alkyl group-containing trimethylenenorbornanes contained in the raffinate at the time of the concentration, the amount of alkyladamantanes (such as methyladamantane) contained in an isomerization reaction liquid can be reduced, so that it is possible to obtain high-purity adamantane.

As the catalyst used for isomerization reaction of trimethylenenorbornane, there may be mentioned an acid catalyst, such as an aluminum chloride catalyst, or a solid catalyst.

With the consideration of troublesomeness of the post treatment after isomerization, the solid catalyst is preferably used, though an aluminum chloride catalyst may be used.

As the solid catalyst, there may be mentioned a solid acid catalyst carrying a metal.

As the solid acid, there may be mentioned zeolites (A-type, L-type, X-type, Y-type, ZSM-5, etc.), sulfated zirconia, silica-alumina and alumina, and hetero polyacids. Above all, a zeolite, particularly Y-type zeolite, is preferred.

As the metal, there may be mentioned metals belonging to Group 8 to Group 10 of the Periodic Table and rhenium. Above all, ruthenium, rhodium, palladium, iridium, platinum and rhenium are preferred. Platinum is more preferred.

The solid catalyst may be prepared by known methods.

For example, a method of preparing a solid catalyst in which a metal is carried on a zeolite includes carrying at least one metal on the zeolite by an ion exchange process or an impregnation process.

In the case of the ion exchange process, the catalyst may be prepared by contacting the zeolite with an aqueous solution of a metal salt or an aqueous solution of a metal complex, in which the metal is one as described above, to ion-exchange the cation thereof (such as $H^+$ and $NH_4^+$), followed by drying and calcination.

In the case of the impregnation process, the catalyst may be prepared by impregnating the above metal to be carried, namely by mixing a zeolite with an aqueous solution of a metal salt or an aqueous solution of a metal complex, followed by evaporation to dryness.

The shape of the solid catalyst is not specifically limited. A catalyst of any desired shape such as powder or granules may be used.

The isomerization of trimethylenenorbornane in the presence of the above solid catalyst may be carried out in the presence of a monocyclic saturated hydrocarbon compound, an aromatic compound, water and/or an alcohol.

As the monocyclic saturated hydrocarbon compound which is allowed to be present, there may be mentioned, for example, cyclopentane, cyclohexane, ethylcyclohexane and methylcyclohexane.

Cyclohexane, ethylcyclohexane or a mixture thereof is particularly preferable.

As the aromatic compound, there may be mentioned, for example, aromatic hydrocarbons such as benzene, toluene, xylene, naphthalene and anthracene; oxygen-containing aromatic compounds such as phenol, benzaldehyde, benzoic acid, benzyl alcohol and anisole; nitrogen-containing aromatic compounds such as aniline and nitrobenzene; and halogen-containing aromatic compounds such as chlorobenzene and bromobenzene.

Among these aromatic compounds, aromatic hydrocarbon compounds such as benzene, toluene, xylene, naphthalene and anthracene are preferred. Particularly preferred is benzene.

As the alcohol, there may be mentioned, for example, monohydric alcohols such as methyl alcohol, isopropyl alcohol, tert-butyl alcohol; and benzyl alcohol and polyhydric alcohols such as ethylene glycol and glycerine.

The amount of these compounds which are allowed to be present is not specifically limited and can be suitably selected according to various situations.

Regarding the reaction conditions for isomerization of trimethylenenorbornane using the solid catalyst, the reaction temperature is generally 150 to 500° C., preferably 200 to 400° C., and the isomerization reaction pressure may be ambient pressure or under an increased pressure.

The reaction mode may be with the use of a flow-type reactor or a batch-type reactor.

When the reaction is performed in a batch-type, the reaction time is about 1 to about 50 hours.

The reaction is preferably carried out in the presence of hydrogen for reasons of improved yield of adamantane.

In the present invention, the reaction product liquid obtained by performing the isomerization in the above-described manner is used as a crystallization raw material and crude adamantane may be separated by crystallization procedures.

The concentration of adamantane in the crystallization raw material is preferably 10 to 40% by mass. The temperature is not specifically limited as long as the temperature is higher than the temperature at which adamantane is entirely dissolved.

When the reaction product liquid having an adamantane concentration of less than 10% by mass is used as the crystallization raw material, it is advantageous to previously concentrate the liquid by distillation, etc.

The reason for this is that the recovery efficiency of adamantane during the crystallization step is reduced when the adamantane concentration is excessively low.

On the other hand, when the adamantane concentration is excessively high, the viscosity of the slurry obtained by the crystallization is so high that it is difficult to perform the succeeding procedures.

In the present invention, the crystallization procedure may be by crystallization by cooling or crystallization by evaporation. Both procedures may be combined if desired.

The crystallization procedure may be performed in the continuous mode or batch mode.

When the crystallization by cooling is performed continuously, the crystallization temperature is generally −20 to 50° C., preferably 0 to 30° C.

When the crystallization temperature is −20° C. or higher, consumption of a large amount of energy for cooling can be avoided. When the temperature is 50° C. or lower, a good recovery efficiency of adamantanes is obtainable.

When the crystallization by cooling is performed in a batch mode, the final temperature is preferably −20 to 50° C. for the same reasons as above, and the final temperature is more preferably adjusted to 0 to 30° C.

The crystallization liquid containing precipitated adamantane is subjected to a solid liquid separation treatment by any ordinary method using a filter cloth or sintered metal, such as by vacuum filtration or centrifugation.

When a single procedure of crystallization fails to give adamantane having the desired or higher purity, the obtained crystals may be dissolved in an ordinary organic solvent for carrying out recrystallization.

In dissolving in such an organic solvent, it is not preferable that the solubility of adamantane in the organic solvent be low.

Examples of such a crystallization solvent, namely ill-suited organic solvent, include alcohols, ketones and carboxylic acids.

In the present invention, the solid liquid separation is followed by a rinsing step in which a wet cake (crude adamantane crystals) obtained by separating a liquid containing trimethylenenorbornane being an unreacted starting material and by-products is rinsed.

Since the wet cake contains liquid trimethylenenorbornane as an unreacted starting material, liquid by-products and so on, it is industrially advantageous that the solid liquid separation step be carried out to remove the liquid so that the wet cake has a liquid content of about 5 to about 50% by mass.

A high liquid content causes reduction of the efficiency for rinsing the wet cake, while a low liquid content causes consumption of much time and energy for the removal of the liquid.

As the rinsing procedure, there may be mentioned, for example, a substituting rinsing in which a solvent is passed through the wet cake after the liquid separation, and a method in which the wet cake is slurried in a solvent and the slurry is then filtered.

As the rinsing solvent, organic compounds having a boiling point of 150° C. or lower may be mentioned.

Examples of such an organic compound include, but not limited to, alcohols such as methanol, ethanol, 1-propanol and isopropyl alcohol; ketones such as acetone, methyl ethyl ketone and diethyl ketone; carboxylic acids such as acetic acid; halogenated compounds such as carbon tetrachloride; aliphatic compounds such as pentane, hexane and heptane; alicyclic compounds such as cyclohexane and ethylcyclohexane; aromatic compounds such as benzene, toluene and xylene; and mixtures thereof.

The organic compound is particularly preferably a middle fraction having a boiling point of not higher than 150° C. obtained from petroleum refining factories or the like (for example, light naphtha or mixtures of benzene, toluene, xylenes, etc. which are obtained from equipments for aromatics and which have not yet been purified) for reasons of cheapness.

A rinsing solvent having a boiling point not higher than 150° C. can make it easy to dry crystals of adamantanes.

The rinsing temperature is −20 to 50° C., preferably 0 to 30° C.

In performing the substituting rinsing, the rinsing solvent is used in an amount of 10 to 300% by mass, preferably 20 to 100% by mass, based on the wet cake.

In making slurry with a rinsing solvent, the amount of the rinsing solvent is 100 to 500% by mass, preferably 150 to 400% by mass, based on the wet cake.

The adamantane crystals can have high purities under the rinsing procedures, in which the rinsing solvent adhering on the crystals is evaporated to dry.

EXAMPLES

The present invention will be described in further detail below by way of Examples. However, the present invention is not limited to those Examples in any way.

Example 1

(1) Catalyst Preparation Step 1,275 Grams of a Y-type zeolite having sodium ions in its cation sites (hereinafter referred to as NaY) were added and suspended in 7 kg of pure water with stirring and the suspension was heated to 60° C.

While continuing the stirring, 8 kg of an aqueous solution of mixed rare earth chlorides (mixed chlorides containing 49% by mass of Ce, 24% by mass of La, 20% by mass of Nd, 5% by mass of Pr and 2% by mass of Sm) [890 g in terms of $RE_2O_3$ (total of $CeO_2+La_2O_3+Nd_2O_3+Pr_2O_3+Sm_2O_3$)] were further added and the mixture was stirred for 2 hours.

The solids were then collected by filtration and washed with 15 kg of pure water.

The washed product was dried and thereafter calcined at 650° C. for 3 hours (primary exchange with mixed rare earths).

The thus calcined powder 340 g was suspended in 2 kg of warm water at 60° C., to which hydrochloric acid was added with stirring until the pH became 5.01.

The thus obtained slurry was mixed with 2 kg of the aqueous solution of mixed rare earth chlorides similar to described above [130.6 g in terms of $RE_2O_3$ (the same as above)] and the mixture was stirred at 60° C. for 2 hours.

The solids were then collected by filtration and washed with 4 kg of pure water (secondary exchange with mixed rare earths).

The thus obtained powder 340 g was suspended again in 2 kg of pure water, to which 340 g of 1.81% by mass aqueous tetrammine-platinum chloride solution were added. The mixture was stirred at 30° C. for 2 hours.

This was filtered and washed, and then dried overnight at 110° C. to obtain an uncalcined solid catalyst of a mixed rare earths-containing Y-type zeolite carrying 1.0% by mass of platinum.

(2) Isomerization Step

In a stainless steel reaction tube, 20 g of the catalyst obtained in (1) above were filled and calcined at 300° C. for 3 hours in the stream of air.

After substitution with nitrogen, hydrogen reduction was carried out at 300° C. for 2 hours under ambient pressure in the stream of hydrogen.

Then, the supply of a raffinate [containing 25% by mass of trimethylenenorbornane (TMN), 4% by mass of methyltrimethylenenorbornane (MTMN), 40% by mass of naphthenes having 8 to 10 carbon atoms, 25% by mass of aromatics having 7 to 9 carbon atoms and 6% by mass of paraffins having 7 to 10 carbon atoms] and hydrogen was started. Thus, isomerization was continuously carried out under conditions of 325° C., 5 MPa, WHSV 0.5 hr$^{-1}$ (based on TMN) and hydrogen/TMN molar ratio of 2.

The results of the isomerization after 50 hours from the start of the feed of the raffinate are shown in Table 1.

[Table 1]

TABLE 1

| | Trimethylene-norbornane (TMN) Conversion (% by mass) | Methyl-trimethylene norbornane (MTMN) (% by mass) | Adamantane (ADM) | | |
| --- | --- | --- | --- | --- | --- |
| | | | Selectivity (% by mass) | Yield (% by mass) | Purity (%) |
| Example 1 | 84.4 | 4.0 | 20.2 | 17.0 | 97.3 |
| Example 2 | 86.3 | 0.79 | 20.3 | 17.5 | 99.1 |
| Example 3 | 85.3 | 11.2 | 20.1 | 17.1 | 95.4 |
| Example 4 | 85.1 | 8.0 | 20.5 | 17.4 | 96.2 |
| Comparative Example 1 | 85.4 | 0.0 | 18.5 | 15.8 | 99.0 |

TMN conversion = [1 − (mass of TMN after reaction)/(mass of TMN before reaction)] × 100
ADM selectivity = [(mass of ADM produced)/(mass of TMN before reaction − mass of TMN after reaction)] × 100
ADM yield = [(mass of ADM produced)/(mass of TMN before reaction)] × 100

(3) Post Treatment Step

600 Grams of the thus obtained isomerized liquid (adamantane (ADM) concentration: 4.3% by mass) were concentrated by atmospheric distillation to an adamantane concentration of 27% by mass.

The concentrated liquid was heated to 120° C. with stirring to dissolve crystallized adamantane and then cooled to 10° C. with stirring to crystallize the adamantane and to obtain a slurry containing crystallized adamantane.

The slurry was then filtered through a 70 μm glass filter to obtain crude adamantane crystals.

The crude adamantane crystals on the 70 μm filter were mixed with isopropyl alcohol for the substituting rinsing by vacuum filtration.

The thus obtained adamantane crystals were air dried to vaporize the isopropyl alcohol and to obtain 40 g of adamantane crystals.

The adamantane crystals were analyzed by gas chromatography to reveal that the purity of the adamantane crystals was 97.3% by mass and that the impurities included 1.1% by mass of unreacted trimethylenenorbornane and 1.6% by mass of by-products.

Example 2

Isomerization was carried out in the same manner as that in Example 1 except that the raffinate was first distilled under atmospheric pressure to obtain a concentrated raffinate having a trimethylenenorbornane concentration of 80% by mass and a methyltrimethylenenorbornane concentration reduced to 0.79% by mass and that the concentrated raffinate was used as the starting material.

The results of the isomerization after 50 hours from the start of the feed of the concentrated raffinate are shown in Table 1.

600 Grams of the thus obtained isomerized liquid (adamantane concentration: 14.0% by mass) were concentrated by atmospheric distillation to an adamantane concentration of 28% by mass.

The concentrated liquid was heated to 120° C. with stirring to dissolve crystallized adamantane and then cooled to 10° C. with stirring to crystallize the adamantane and to obtain a slurry containing crystallized adamantane.

The slurry was filtered through a 70 µm glass filter to obtain crude adamantane crystals.

The crude adamantane crystals on the 70 µm filter were mixed with isopropyl alcohol for the substituting rinsing by vacuum filtration.

The thus obtained adamantane crystals were air dried to vaporize the isopropyl alcohol and to obtain 49 g of adamantane crystals.

The adamantane crystals were analyzed by gas chromatography to reveal that the purity of the adamantane crystals was 99.1% by mass and that the impurities included 0.5% by mass of unreacted trimethylenenorbornane and 0.4% by mass of by-products.

Example 3

Isomerization was carried out in the same manner as that in Example 2 except that the raffinate was first distilled under atmospheric pressure to obtain a concentrated raffinate having a trimethylenenorbornane concentration of 81% by mass and a methyltrimethylenenorbornane concentration of 11.2% by mass and that the concentrated raffinate was used as the starting material.

The results of the isomerization after 50 hours from the start of the feed of the concentrated raffinate are shown in Table 1.

600 Grams of the thus obtained isomerized liquid (adamantane concentration: 13.9% by mass) were concentrated by atmospheric distillation to an adamantane concentration of 28% by mass.

The concentrated liquid was post treated in the same manner as that in Example 2 to obtain 49 g of adamantane crystals.

The adamantane crystals were analyzed by gas chromatography to reveal that the purity of the adamantane crystals was 95.4% by mass and that the impurities included 1.2% by mass of unreacted trimethylenenorbornane and 3.4% by mass of by-products.

Example 4

Isomerization was carried out in the same manner as that in Example 2 except that the raffinate was first distilled under atmospheric pressure to obtain a concentrated raffinate having a trimethylenenorbornane concentration of 79.8% by mass and a methyltrimethylenenorbornane concentration of 8.0% by mass and that the concentrated raffinate was used as the starting material.

The results of the isomerization after 50 hours from the start of the feed of the concentrated raffinate are shown in Table 1.

600 Grams of the thus obtained isomerized liquid (adamantane concentration: 13.9% by mass) were concentrated by atmospheric distillation to an adamantane concentration of 28% by mass.

The concentrated liquid was post treated in the same manner as that in Example 2 to obtain 47 g of adamantane crystals.

The adamantane crystals were analyzed by gas chromatography to reveal that the purity of the adamantane crystals was 96.2% by mass and that the impurities included 1.0% by mass of unreacted trimethylenenorbornane and 2.8% by mass of by-products.

Comparative Example 1

Commercially available dicyclopentadiene (purity: 95% by mass, manufactured by Zeon Corporation) was hydrogenated in the conventional manner to obtain trimethylenenorbornane (purity 95% by mass). This was dissolved in ethylcyclohexane to obtain an ethylcyclohexane solution having a trimethylenenorbornane concentration of 80% by mass.

Isomerization was carried out in the same manner as that in Example 1 except that the ethylcyclohexane solution was used as the starting material.

The results of the isomerization after 50 hours from the start of the feed of the ethylcyclohexane solution are shown in Table 1.

500 Grams of the thus obtained isomerized liquid (adamantane concentration: 12.6% by mass) were concentrated by atmospheric distillation to an adamantane concentration of 26% by mass.

The concentrated liquid was heated to 120° C. with stirring to dissolve crystallized adamantane and then cooled to 10° C. with stirring to crystallize the adamantane and to obtain a slurry containing crystallized adamantane.

The slurry was filtered through a 70 µm glass filter to obtain crude adamantane crystals.

The crude adamantane crystals on the 70 µm filter were mixed with isopropyl alcohol for the substituting rinsing by vacuum filtration.

The thus obtained adamantane crystals were air dried to vaporize the isopropyl alcohol and to obtain 37 g of adamantane crystals.

The adamantane crystals were analyzed by gas chromatography to reveal that the purity of the adamantane crystals was 99.0% by mass and that the impurities included 0.6% by mass of unreacted trimethylenenorbornane and 0.4% by mass of by-products.

The results shown in Table 1 indicate that even when a cheap raffinate is used as a starting material for isomerization, it is possible to obtain adamantane with the same or greater yield as compared with isomerization using trimethylenenorbornane obtained by hydrogenating dicyclopentadiene.

INDUSTRIAL APPLICABILITY

With the process of the present invention, it is not necessary to use expensive dicyclopentadiene and, also, it is possible to omit a step of hydrogenating dicyclopentadiene for the preparation of trimethylenenorbornane and to produce high-purity adamantane at a low cost and with a high efficiency.

The invention claimed is:

1. A process for producing adamantane, comprising: isomerizing trimethylenenorbornane that is present in a raffinate obtained from a platfinate.

2. The process for producing adamantane as defined in claim 1, wherein the isomerization is performed after concentrating trimethylenenorbornane contained in the raffinate.

3. The process for producing adamantane as defined in claim 2, wherein the isomerization is performed after concentrating trimethylenenorbomane contained in the raffinate and after reducing the amount of alkyl group-containing trimethylenenorbomane.

4. The process for producing adamantane as defined in claim 1, wherein the isomerization is conducted with a solid catalyst.

* * * * *